(12) United States Patent
Miura et al.

(10) Patent No.: US 9,265,671 B2
(45) Date of Patent: Feb. 23, 2016

(54) ABSORBENT ARTICLE HAVING A GRAPHIC VISIBLE THROUGH BODY CONTACTING SURFACE

(71) Applicant: The Procter & Gamble Company, Cincinnati, OH (US)

(72) Inventors: Tsunetoshi Miura, Kobe Hyogo (JP); Kensuke Ito, Kobe Hyogo (JP); Akiko Sasaki, Nishinomiya Hyogo (JP); Yoshiko Nakao, Nishinomiya Hyogo (JP); Shuri Kondo, Ashiya Hyogo (JP); Koichi Tomi, Kobe Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 240 days.

(21) Appl. No.: 13/783,990

(22) Filed: Jun. 5, 2013

(65) Prior Publication Data

US 2013/0281953 A1 Oct. 24, 2013

Related U.S. Application Data

(60) Continuation of application No. 13/102,697, filed on May 6, 2011, now Pat. No. 8,629,315, which is a division of application No. 11/894,851, filed on Aug. 22, 2007, now Pat. No. 7,959,620, which is a (Continued)

(51) Int. Cl.
*A61F 13/42* (2006.01)
*A61F 13/514* (2006.01)
(Continued)

(52) U.S. Cl.
CPC ......... *A61F 13/51496* (2013.01); *A61F 13/472* (2013.01); *A61F 13/4755* (2013.01);
(Continued)

(58) Field of Classification Search
CPC ......... A61F 13/02; A61F 13/15; A61F 13/47; A61F 13/51; A61F 13/514; A61F 13/551; A61F 13/56; A61F 13/42
See application file for complete search history.

(56) References Cited

U.S. PATENT DOCUMENTS 5,897,541 A 4/1999 Uitenbroek et al.
6,074,376 A 6/2000 Mills
(Continued)

FOREIGN PATENT DOCUMENTS

GB 2 354 449 A 3/2001
JP 3021237 B2 6/1989
(Continued)

OTHER PUBLICATIONS

English translation of description for JP 2003-99786 A (Suzuki et al) (2003). http://www4.ipdl.inpit.go.jp.*
(Continued)

*Primary Examiner* — Melanie Hand
(74) *Attorney, Agent, or Firm* — George H. Leal; Andrew J. Hagerty

(57) ABSTRACT

An absorbent article for feminine hygiene, comprising: a body contacting layer; a garment contacting layer; and an absorbent core disposed between the body contacting layer and the garment contacting layer. The absorbent core has a core edge. The core edge defines a core region within the core edge and an outer region outside the core region. The body contacting layer and the garment contacting layer extend outward into the outer region and joined together in the outer region. The garment contacting layer may have a graphic printed on the body facing surface or the body contacting layer may have a graphic printed on the garment facing surface. The body contacting layer has a first light transmittance so that the graphic can be seen through the body contacting layer.

27 Claims, 3 Drawing Sheets

Related U.S. Application Data continuation of application No. 10/603,522, filed on Jun. 25, 2003, now abandoned.

(60) Provisional application No. 60/396,115, filed on Jul. 16, 2002.

(51) Int. Cl.
*A61F 13/475* (2006.01)
*A61F 13/511* (2006.01)
*A61F 13/84* (2006.01)
*A61F 13/513* (2006.01)
*A61F 13/472* (2006.01)
*A61F 13/15* (2006.01)

(52) U.S. Cl.
CPC ......... *A61F13/511* (2013.01); *A61F 13/51394* (2013.01); *A61F 13/84* (2013.01); *A61F 2013/15243* (2013.01); *A61F 2013/8497* (2013.01)

(56) References Cited

U.S. PATENT DOCUMENTS

| | | |
|---|---|---|
| 6,231,555 B1 | 5/2001 | Lynard |
| 6,482,192 B2 | 11/2002 | Haarer et al. |
| 6,569,136 B1 | 5/2003 | Tao et al. |
| 6,695,697 B1 | 2/2004 | Okada |
| 6,949,689 B2 | 9/2005 | Noda et al. |
| 2001/0031954 A1 | 10/2001 | Jordan et al. |
| 2003/0065299 A1 | 4/2003 | Carlucci et al. |
| 2003/0109839 A1 | 6/2003 | Costea et al. |
| 2003/0114809 A1 | 6/2003 | Gagliardi et al. |
| 2003/0207091 A1 | 11/2003 | Nair et al. |
| 2004/0170813 A1 | 9/2004 | Digiacomantonio et al. |

FOREIGN PATENT DOCUMENTS

| | | |
|---|---|---|
| JP | 2003/199786 A | 7/2003 |
| JP | H07/88128 A | 7/2003 |
| WO | WO 91/19471 | 12/1991 |
| WO | WO 95/07674 A2 | 3/1995 |
| WO | WO 96/23469 | 8/1996 |
| WO | WO 00/65083 | 11/2000 |

OTHER PUBLICATIONS

"Color Digitalization in Each Color Specification System".
PCT International Search Report dated Dec. 19, 2003.

* cited by examiner

ABSORBENT ARTICLE HAVING A GRAPHIC VISIBLE THROUGH BODY CONTACTING SURFACE

FIELD OF THE INVENTION

The present invention relates to absorbent articles. More particularly, the present invention relates to an absorbent article having a graphic which is visible through the body contacting surface.

BACKGROUND OF THE INVENTION

Absorbent articles such as sanitary napkins, pantiliners and incontinent pads are devices that are typically worn in the crotch region of an undergarment. More specifically, sanitary napkins and pantiliners, for example, are worn by women in a pair of panties that is normally positioned between the wearer's legs, adjacent to the perineum area. Sanitary napkins and pantiliners are designed to absorb and retain body fluids or discharges (e.g., urine and menses) from the body of women and to prevent body and clothing from soiling. A wide variety of shapes and dimensions of sanitary napkins and pantiliners is currently used by women for the collection of body fluids.

The menstrual period is very troublesome for women and almost all the women are in a depressed mood during the period. Conventional sanitary napkins have a white color or a simple combination of light colors to provide a clean appearance. Because of the appearance, such sanitary napkins normally do not affect women's feeling, i.e., they do not help to decrease or change women's depressed mood during the menstruation period.

Japanese Utility Model Registration No. 3021237 discloses a sanitary napkin having wings that are provided with a color or pattern on both the body contacting surface and the garment contacting surface. This publication teaches that by using a color or pattern of the sanitary napkin which is similar to that of the undergarment, the use of the sanitary napkin can not be easily recognized from the outside by others. This publication, however, is silent about a concrete structure of the sanitary napkin that can be practically manufactured nor a design that can affect the women's mood in the menstruation period. It is because this publication merely focuses on the similarity of the color or pattern between the sanitary napkin and the undergarment, and it does not recognize the need for improving women's depressed mood through the design of sanitary napkin during the menstruation period.

Thus, there is a need for an absorbent article that can provide an emotional benefit to users, and thus decrease users' melancholic mood without distress or inconvenience.

SUMMARY OF THE INVENTION

The invention is directed to an absorbent article, which is preferably a sanitary napkin or a pantiliner, comprising: a body contacting layer; a garment contacting layer; and an absorbent core disposed between the body contacting layer and the garment contacting layer. The absorbent core has a core edge. The core edge defines a core region within the core edge and an outer region outside the core region. The body contacting layer and the garment contacting layer extend outward into the outer region and joined together in the outer region.

In one aspect of the invention, the garment contacting layer has a graphic printed on the body facing surface at least in a portion of the outer region.

In another aspect of the invention, the body contacting layer has a graphic printed on the garment facing surface at least in a portion of the outer region.

The body contacting layer has a first light transmittance so that the graphic can be seen through the body contacting layer in the outer region.

The foregoing answers the need for an absorbent article that can provide an emotional benefit to users, and thus decrease users' melancholic mood without distress or inconvenience.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

Figure 1:
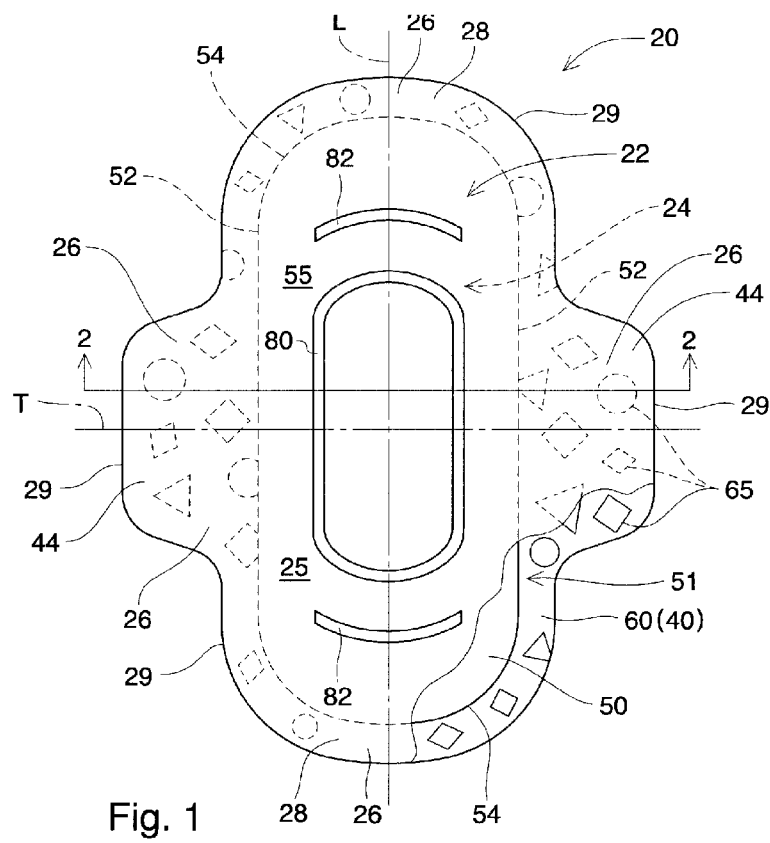
FIG. 1 is a top plan view of a sanitary napkin which is one preferred embodiment of the present invention.

All cited references are incorporated herein by reference in their entireties. Citation of any reference is not an admission regarding any determination as to its availability as prior art to the claimed invention.

Herein, "comprise" and "include" mean that other elements and/or other steps which do not affect the end result can be added. Each of these terms encompasses the terms "consisting of" and "consisting essentially of".

Herein, "absorbent article" refers to articles which absorb and contain body exudates or discharges such as body fluids, and is intended to include sanitary napkins, pantiliners, diapers, and incontinence pads (and other articles worn in the crotch region of a garment).

Herein, "disposable" refers to articles which are intended to be discarded after a single use, composted, or otherwise disposed of in an environmentally compatible manner. (That is, they are not intended to be laundered or otherwise restored or reused as an absorbent article.)

Herein, "sanitary napkin" refers to articles which are worn by females adjacent to the pudendal region which are intended to absorb and contain the various exudates which are discharged from the body (e.g., blood, menses, and urine).

Herein, "joined" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

Herein, "body facing surface" refers to surfaces of absorbent articles and/or their component members which face the body of the wearer, while the term "garment facing surface" refers to the opposite surfaces of the absorbent articles and/or their component members that face away from the wearer when the absorbent articles are worn. Absorbent articles and components thereof, including the topsheet, backsheet, absorbent core, and any individual layers of their components, have a body facing surface and a garment facing surface.

Herein, "graphic" refers to an image or a design that is constituted by a figure (i.e., a line(s)), a symbol or character, a color difference or transition of at least two colors, or the like. The graphic preferably has an aesthetic image or design that can provide emotional benefit(s) when the absorbent article of the invention is looked or viewed by users. Such emotional benefits include, but not limited to, a relaxed feeling, a happy or pleasant feeling, an encouraged feeling, and the like. Preferred aesthetic images or designs include, but not limited to, plants such as flowers (e.g., a dandelion), pretty animals such as cats, cartoon characters, seasonal things or goods such as snowmen, landscapes, and the like. The graphic may further include other design or information than the aesthetic image, for example, a usage information about the size of the absorbent article, an indication of the front/back of the absorbent article, and the like.

FIG. 1 is a top plan view of a sanitary napkin 20 (i.e., a disposable absorbent article) which is one preferred embodiment of the present invention. Referring to FIG. 1, the sanitary napkin 20 (and its component members) has a body facing surface 22, and a garment facing surface 24 opposed to the body facing surface 22. The sanitary napkin 20 shown in FIG. 1 is viewed from the body facing surface 22. The sanitary napkin 20 has a circumferential edge 29 which defines the outermost edge of the sanitary napkin 20.

The sanitary napkin 20 has two centerlines, a longitudinal centerline L and a transverse centerline T. Herein, "longitudinal" refers to a line, axis or direction in the plane of the sanitary napkin 20 that is generally aligned with (e.g., approximately parallel to) a vertical plane which bisects a standing wearer into left and right body halves when the sanitary napkin 20 is worn. Herein, "transverse" or "lateral", are interchangeable, and refer to a line, axis or direction which lies within the plane of the sanitary napkin 20 that is generally perpendicular to the longitudinal direction.

Figure 2:
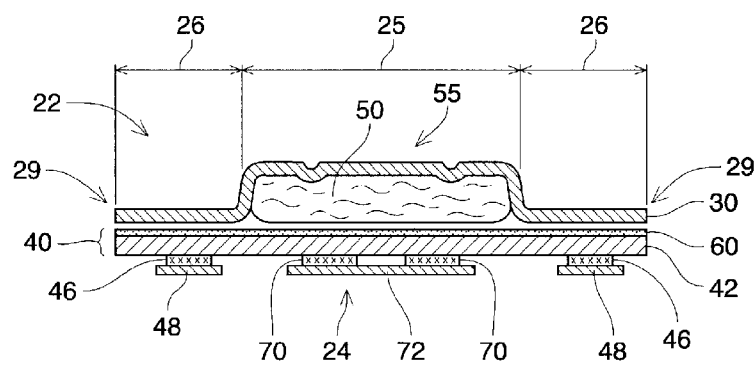
FIG. 2 is a cross-sectional view of the sanitary napkin shown in FIG. 1, taken along the line 2-2.

FIG. 2 is a cross-sectional view of the sanitary napkin 20 shown in FIG. 1, taken along the line 2-2. The sanitary napkin 20 includes three primary components. These include a body contacting layer 30 (typically known as a liquid permeable topsheet), a garment contacting layer 40 (typically known as a liquid impermeable backsheet), and an absorbent core 50 disposed between the body contacting layer 30 and the garment contacting layer 40. The top surface of the body contacting layer 30 forms the body facing surface 22 of the sanitary napkin 20, while the bottom surface of the garment contacting layer 40 forms the garment facing surface 24 of the sanitary napkin 20.

As shown in FIG. 1, the absorbent core 50 has a core edge 51 which preferably includes longitudinal side edges 52 and lateral end edges 54. The core edge 51 defines a core region 25 within the core edge 51, and an outer region 26 outside the core region 25 and inside the circumferential edge 29 of the sanitary napkin 20. A main body portion 55 is constituted in the core region 25 by these three primary components 30, 40 and 50 of the sanitary napkin 20.

The absorbent core 50 may be manufactured in a wide variety of sizes and shapes. The core edge 51 of the absorbent core 50 thus can take any shape in its top plan view. Preferred shapes for the core edge 51 include an oval, a rectangle, an hourglass, and a combination of the oval and rectangle such as the one shown in FIG. 1.

The body contacting layer 30 and the garment contacting layer 40 extend outward into the outer region 26. These two layers 30 and 40 preferably extend in both the longitudinal and transverse directions to reach the circumferential edge 29 of the sanitary napkin 20. These two layers 30 and 40 are joined together in the outer region 26. These two layers 30 and 40 can be joined any means (e.g., an adhesive) known in the art. However, such means should not significantly affect the light transmittance (discussed hereinafter) of the body contacting layer 30 (preferably and the garment contacting layer 40). Preferably, these portions of the body contacting layer 30 and the garment contacting layer 40 are joined using adhesives (not shown in Figs.) over substantially the entire portions that extend beyond the core edge 52 of the absorbent core 50. In a preferred embodiment, the body contacting layer 30 and garment contacting layer 40 are densified by an application of pressure or heat and pressure in the outer region 26 to form a crimp seal.

Figure 3:
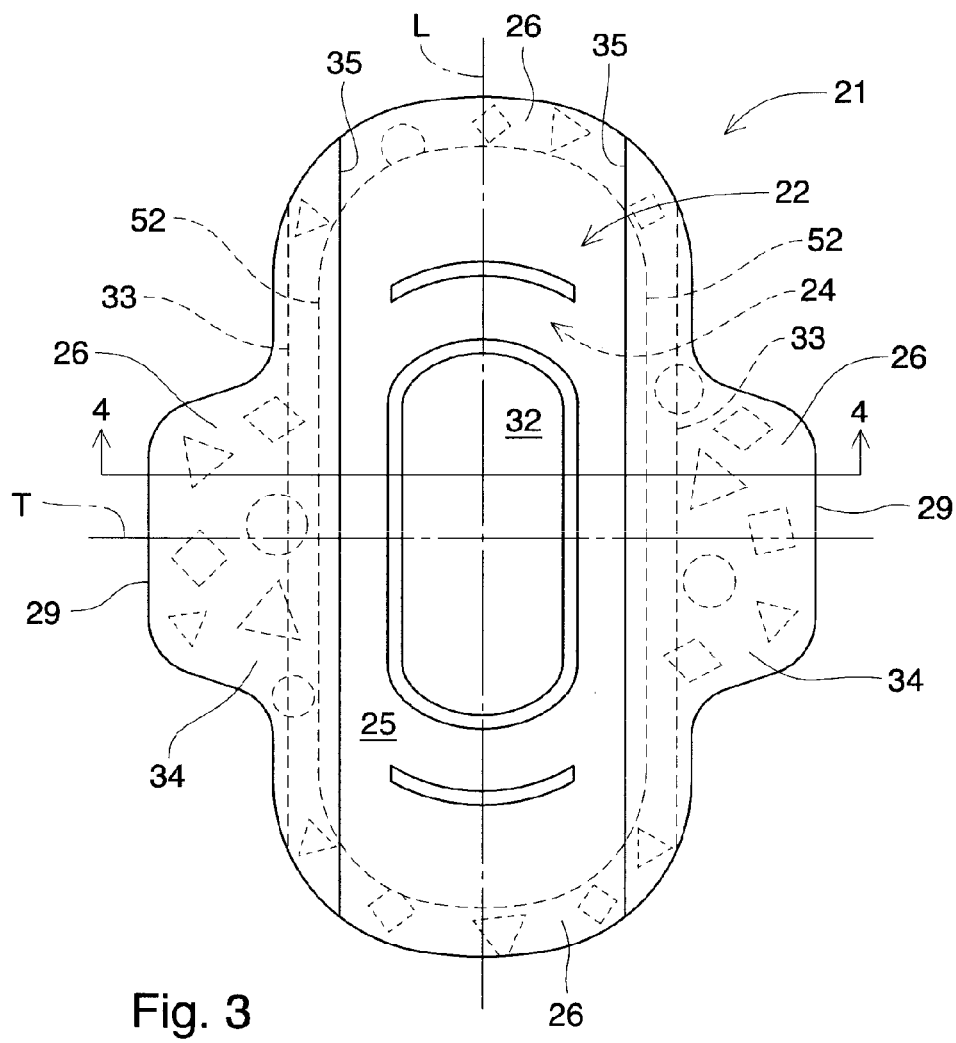
FIG. 3 is a top plan view of a sanitary napkin which is another preferred embodiment of the present invention.

FIG. 3 is a top plan view of a sanitary napkin 21 which is another preferred embodiment of the present invention. Referring to FIG. 3, the sanitary napkin 21 basically has a similar structure to that of the sanitary napkin 20 shown in FIG. 1 except the body contacting layer 30. Specifically, compared with the sanitary napkin 20 shown in FIG. 1, the sanitary napkin 21 has a body contacting layer 30' which includes a liquid permeable topsheet layer 32 disposed in the core region 25, and graphic protection layers 34 disposed in the outer region 26.

Figure 4:
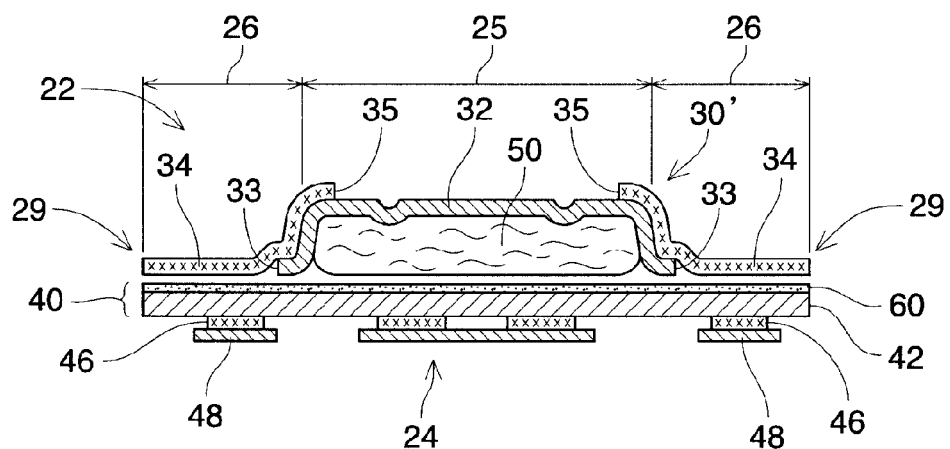
FIG. 4 is a cross-sectional view of the sanitary napkin shown in FIG. 3, taken along the line 4-4.

FIG. 4 is a cross-sectional view of the sanitary napkin 21 shown in FIG. 3, taken along the line 4-4. Referring to FIG. 4, the topsheet layer 32 is primarily disposed in the core region 25 to cover the body facing surface 22 of the absorbent core 50. The topsheet layer 32 transversely extends over the core edge 52 and slightly into the outer region 26. The topsheet layer 32 has longitudinal side edges 33 which end in the outer region 26. The graphic protection layer 34 is primarily disposed in the outer region 26. The graphic protection layer 34 overlays the longitudinal side edge 33 of the topsheet layer 32 in the outer region 26 and extends outward to the circumferential edge 29 of the sanitary napkin 21. The graphic protection layer 34 has longitudinal inner edges 35 starting above the absorbent core 50 in the core region 25.

In this embodiment, since two different materials can be used for the body contacting layer 30' (i.e., the topsheet layer 32 and the graphic protection layers 34), a more suitable choice can be made on the two materials (compared with the sanitary napkin 20 shown in FIG. 1). For example, a material which has a suitable light transmittance can be selected for the graphic protection layers 34 in the outer region 26, while another material which has a suitable liquid permeability can be selected for the topsheet layer 32 in the core region 25. This is beneficial since it is not always easy to find one material that can meet the both requirements for the body contacting layer 30 (e.g., appropriate light transmittance and liquid permeability).

The garment contacting layer 40 has a graphic 65 printed on the body facing surface 22 at least in a portion of the outer region 26. Preferably, the graphic 65 is printed at least in the whole area of the outer region 26. More preferably, for simplicity of manufacture, the graphic 65 is printed on the whole body facing surface 22 of the garment contacting layer 40, as shown in FIG. 2 wherein the graphic 65 is shown as a graphic layer (or a printed layer) 60 on the body facing surface 22 of the garment contacting layer 40. In this embodiment, the garment contacting layer 40 includes the graphic layer 60 on the body facing surface 22.

The graphic layer 60 may be formed by either only a printed ink or a substrate layer having an ink printed on its one surface. In one preferred embodiment, the graphic layer 60 is formed by only a printed ink layer disposed on the body facing surface 22 of the garment contacting layer 40. In an alternative preferred embodiment, the graphic layer 60 is formed by a substrate layer having an ink printed on the body facing surface 22 of the substrate layer. In this embodiment, the substrate layer having the ink printed is a part of the garment contacting layer 40.

More specifically, the garment contacting layer 40 may include, at least in the outer region 26, two (or more) layers of materials which are preferably joined together through an adhesive (or an application of pressure or heat and pressure) to form a laminate. In one embodiment, the garment contacting layer 40 includes two layer materials, i.e., a graphic layer 60 (or a substrate layer for the graphic 65) and a liquid impermeable layer 42 as shown in FIGS. 2 and 4. The graphic layer 60 having the graphic 65 printed is disposed on the body facing surface 22 of the liquid impermeable layer 42 at least in the outer region 26, preferably in both the core region 25 and the outer region 26 as shown in FIGS. 2 and 4. Preferred materials for the graphic layer 60 include, but not limited to, a thin plastic film, a nonwoven web and a tissue wherein the graphic 65 is printed on its body facing surface 22. The graphic layer 60 is disposed at least in the outer region 26, preferably in both the core region 25 and the outer region 26 (in that embodiment, the whole body facing surface 22 of the liquid impermeable layer 42 is covered by the graphic layer 60).

In one alternative embodiment, the graphic 65 is printed on the garment facing surface 24 of the body contacting layer 30 at least in a portion of the outer region 26 (not shown in Figs.). If desired, such a graphic can be printed on the garment facing surface 24 of the body contacting layer 30 in both the core region 25 and the outer region 26 (not shown in Figs.). In a preferred embodiment, the graphic protection layer 34 has a graphic 65 printed (or a graphic layer) on the garment facing surface 24 (not shown in Figs.)

In these embodiments, since the graphic 65 is disposed between (and covered by) the body contacting layer 30 and the garment contacting layer 40, the graphic 65 which has been printed does not directly contact the skin of wearer nor her undergarment. This is beneficial because the ink of the graphic 65 is not directly rubbed by the skin or the undergarment and thus a removal of the ink (and a transfer of the ink to other portion) can be prevented.

The graphic 65 can be printed by any conventional printing methods or technologies known in the art, including, but not limited to, a gravure printing, a flexo printing, an offset printing, an ink jet printing, and the like. In a preferred embodiment, the graphic 65 is printed on the whole body facing surface 22 of the garment contacting layer 40 (as shown in FIGS. 2 and 4) by a gravure printing.

The body contacting layer 30 (or the graphic protection layer 34 in the embodiment shown in FIGS. 3 and 4) has a first light transmittance (LT1) so that the graphic 65 printed on the body facing surface 22 of the garment contacting layer 40 (or on the garment facing surface 24 of the graphic protection layer 34) can be seen through the body contacting layer 30 in the outer region 26. (In FIG. 1, the graphic 65 which is seen through the garment contacting layer 40 is indicated by the dotted lines.) In order to effectively affect women's mood in the menstruation period, the material used for the body contacting layer 30 needs to have an appropriate range of light transmittance in the outer region 26. In a preferred embodiment, the first light transmittance (LT1) of the body contacting layer 30 in the outer region 26 is at least about 10%, preferably about 45% (i.e., in a range of about 45-100%), and more preferably about 85% (i.e., in a range of about 85-100%). In addition, the first light transmittance (LT1) of the body contacting layer 30 in the core region 25 is preferably less than about 80%, more preferably less than about 70%. This is preferred to prevent body fluids absorbed in the core region 25 from being seen through the body contacting layer 30.

Since users (or women) can see the graphic 65 at least through the body contacting layer 30 (or the graphic protection layer 34 in the embodiment shown in FIGS. 3 and 4), the sanitary napkin 20 can provide an emotional benefit to women before uses, and thus decrease women's melancholic mood.

In addition, the garment contacting layer 40 preferably has a second light transmittance (LT2) so that the graphic 65 on the body facing surface 22 (or on the garment facing surface 24 of the graphic protection layer 34) can also be seen through the garment contacting layer 40. In order to further effectively affect women's mood in the menstruation period, the material used for the garment contacting layer 40 needs to have an appropriate range of light transmittance. In a preferred embodiment, the second light transmittance (LT2) is at least about 10%, preferably about 45% (i.e., in a range of about 45-100%), and more preferably about 85% (i.e., in a range of about 85-100%).

In this embodiment, since users can additionally see the graphic 65 through the garment contacting layer 40, the sanitary napkin 20 can additionally provide an emotional benefit to women, and thus decrease women's melancholic mood.

In one preferred embodiment, the difference between the first and second light transmittances (LT1 and LT2) is less than about 70%, preferably about 50%, and more preferably about 10%. By using the materials which have similar light transmittances for the body contacting layer 30 and the garment contacting layer 40, the graphic 65 can be seen similarly (or with a similar degree or intensity) through both the body contacting layer 30 and the garment contacting layer 40. This similarity may be preferred since the graphic 65 can be seen naturally by users.

Alternatively, if desired, the difference between the first and second light transmittances (LT1 and LT2) can be greater than about 10%, preferably about 50%, and more preferably about 70%.

In a preferred embodiment, the sanitary napkin 20 has the Hunter Lab Total Color Difference (HLTCD) between the outer region and the core region of about 0.5-73, preferably about 6-65, more preferably about 9-55.

The HLTCD generally indicates a color appearance between two objects. The human eye-brain impression (i.e., the visual perception of human) is also considered in the HLTCD. The HLTCD is preferably within the above ranges to make women's emotion effectively stable while maintaining an appropriate range of the visibility of the graphic 65 to be seen through the body contacting layer 30.

A preferred method for measuring the light transmittances (LT1 and LT2) and the HLTCD will be described in the "Test Methods" section.

The body contacting layers 30 and 30' are preferably compliant, soft feeling, and non-irritating to the wearer's skin. Further, the body contacting layer 30 (or the topsheet layer 32 in the embodiment shown in FIGS. 3 and 4) is liquid permeable or pervious, permitting body fluids (e.g., menses and/or urine) to readily penetrate through its thickness. A suitable liquid permeable material for the body contacting layer may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the body contacting layer 30 includes a nonwoven web, the web may be manufactured by a wide number of known techniques. For example, the web may be spunbonded, carded, wet-laid, melt-blown, hydroentangled, combinations of the above, or the like.

A particularly suitable body contacting layer for use in the sanitary napkins disclosed includes an apertured formed film. Apertured formed films are preferred for the body contacting layer 30 because they are pervious to body fluids and, if properly apertured, have a reduced tendency to allow liquids to pass back through and rewet the wearer's skin. Thus, the body facing surface of the formed film (i.e., the body facing surface 22 of the sanitary napkin) remains dry, thereby reducing body soiling and creating a more comfortable feel for the wearer.

Preferably, the body facing surface 22 of the body contacting layer 30 is hydrophilic at least in the core region 25 so that liquids will be transferred through the body contacting layer 30 more readily. If the body contacting layer is made of a hydrophobic material, at least the upper surface (i.e., the body facing surface 22) of the body contacting layer 30 is treated to be hydrophilic so that body fluids will transfer through the body contacting layer 30 more rapidly. This diminishes the likelihood that menstrual fluid will flow off the body contacting layer rather than flowing into and being absorbed by the absorbent core. The body facing surface 22 of the body contacting layer 30 can be made hydrophilic by treating it with a surfactant. A preferred material for the body contacting layer 30 is a macroscopically expanded, three-dimensional formed polyethylene film. One preferred material for the body contacting layer 30 is available from Tredegar Film Products, Indiana, USA under Code No. X-27121.

Preferably, the body contacting layer 30 in the outer region 26 has a hydrophobic nature to prevent body fluids discharged at the core region 25 from wicking therethrough (towards the circumferential edge 29 of the sanitary napkin 20). This prevents the body contacting layer 30 in the outer region 26 from being soiled by body fluids which tend to wick through the body contacting layer 30 toward the circumferential edge 29 of the sanitary napkin 20 due to a capillary force. Thus, this design can also prevent body fluids from leaking from the circumferential edge 29 of the sanitary napkin 20.

The graphic protection layer 34 shown in FIGS. 3 and 4 is also preferably compliant, soft feeling, and non-irritating to the wearer's skin. Preferred materials for the graphic protection layer 34 include nonwoven webs, woven webs, plastic films, polymer materials for coating (e.g., a silicone compound), and the like. Suitable woven and nonwoven materials can be comprised of natural fibers, synthetic fibers or a combination of natural and synthetic fibers. The graphic protection layer 34 can be either hydrophobic or hydrophilic. Preferably, the graphic protection layer 34 is hydrophobic.

A particularly suitable graphic protection layer for use in the sanitary napkins 20 and 21 includes a nonwoven web. Such a web may be spunbonded, carded, wet-laid, melt-blown, hydroentangled, combinations of the above, or the like. Nonwoven webs are preferred for the graphic protection layer 34 because they can provide a soft visibility of the graphic 65 (or a slightly blurred image of the graphic 65) while also providing a soft touch, feel and/or smoothness to the skin.

Preferably, the graphic protection layer 34 has a hydrophobic nature to prevent body fluids discharged at the topsheet layer 32 from wicking therethrough (towards the circumferential edge 29 of the sanitary napkin 20). This prevents the graphic protection layer 34 from being soiled by body fluids which tend to wick through the graphic protection layer 34 toward the circumferential edge 29 of the sanitary napkin 21 due to a capillary force. Thus, this design can also prevent body fluids from leaking from the circumferential edge 29 of the sanitary napkin 21. A preferred material for the graphic protection layer 34 is a hydrophobic spunbonded nonwoven web made by bi-component fibers having polyethylene/polypropylene for sheath/core, which is available from Chisso Corporation, Tokyo, Japan under Code No. EB7120.

The garment contacting layer 40 is impervious to body fluids and is preferably manufactured from a thin plastic film, although other flexible liquid impervious materials may also be used. Herein, "flexible" refers to materials which are compliant and will readily conform to the general shape and contours of the human body. The garment contacting layer 40 prevents the body fluids absorbed and contained in the absorbent core 50 from wetting articles which contact the absorbent article such as bed sheets, pants, pajamas and undergarments. The garment contacting layer 40 may thus include a woven or nonwoven material, polymeric films such as thermoplastic films of polyethylene or polypropylene, or composite materials such as a film-coated nonwoven material.

The garment contacting layer 40 can include a single layer material, or two or more layers of materials. The garment contacting layer 40 preferably has a thickness of from about 0.012 mm (0.5 mil) to about 0.051 mm (2.0 mils). In a preferred embodiment, the garment contacting layer 40 is a single layer polyethylene film. Such a preferred polyethylene film is available from Daedong Co. Ltd., KyungBuk-Do, Korea, under Code No. DNF-0417C.

The garment contacting layer 40 preferably has a microporous structure which can permit vapors to escape from the absorbent core (often called "breathable backsheet") while still preventing body fluids from passing through the garment contacting layer 40. A preferred microporous polyethylene film is available from Mitsubishi Chemical Corporation, Tokyo, Japan, under Code No. NAP. The size of the garment contacting layer is dictated by the size of the absorbent core 50 and the exact absorbent article design selected.

The garment contacting layer 40 can be embossed and/or matte finished to provide a more clothlike appearance.

In preferred embodiments, the sanitary napkin 20 includes an optional pair of flaps (or wings) 44 which are formed by the transversely extended portion of the body contacting layer 30 and the garment contacting layer 40 in the outer region 26 as shown in FIG. 1. The flaps 44 extend outward from at least the central region of the sanitary napkin 20. It should be noted that these flaps 44 are formed in the outer region 26, and preferably have the graphic 65 visible through the body contacting layer 30 (even they have an additional layer inserted therein as flexure-resistance).

Preferably, as shown in FIGS. 1-4, the flaps 44 are integral with the main body portion 55 (i.e., the flaps 44 comprise integral extensions of the body contacting layer 30 and the garment contacting layer 40 from the main body portion 55). In other alternative embodiments, the flaps 24 can be formed by separate members which are joined to the main body portion 55 of the sanitary napkin 20 in any suitable manner. The flaps 44 are each joined to (or associated with) the main body portion 55 along a juncture, typically a longitudinally-oriented (or "longitudinal") juncture (not shown in Figs.).

The flaps 44 can be in any suitable configuration. Suitable flaps are described in U.S. Pat. No. 5,389,094 issued to Lavash, et al. on Feb. 14, 1995; and U.S. Pat. No. 5,558,663 issued to Weinberger, et al. on Sep. 24, 1996.

In a preferred embodiment, an acquisition layer or a secondary topsheet (not shown in Figs.) is additionally disposed between the body contacting layer 30 (or 30') and the absorbent core 50. The acquisition layer quickly transports discharged body fluids received by the body contacting layer 30 to other parts of the acquisition layer and the absorbent core 50, although it may temporarily hold such fluids until they can be absorbed by the absorbent core 50. The distribution function of the acquisition layer is of particular importance in order to more fully utilize the capacity of the absorbent core 50. Thus, while the acquisition layer may comprise a wide variety of absorbent materials, it preferably comprises a fibrous material that can rapidly transport fluid and not collapse upon being wetted so that the acquisition layer can effectively acquire and distribute second and successive fluids.

The acquisition layer can be made from any materials which have fluid transportation functions known in the art. The acquisition layer may, for example, be comprised of woven, nonwoven or tissue materials. The fibers or other components of these materials may be synthetic or natural, or partially synthetic and partially natural. Suitable synthetic fibers include polyester, polypropylene, polyethylene, nylon, viscous rayon, or cellulose acetate fibers. Suitable natural fibers include cotton, cellulose, or other natural fibers.

In one preferred embodiment, the acquisition layer is an air laid tissue material which is available from Concert GmbH, Falkenhagen, Germany under Code No. GH082. In another preferred embodiment, the acquisition layer is a hydrophilic spunbonded nonwoven material of polyethylene, which is available from BBA/Linotec, Aschersleben, Germany, under Code No. Corolind HDPE T27 AXC.

The absorbent core 50 is capable of receiving, absorbing or retaining body fluids discharged. The absorbent core 50 is preferably compressible, conformable, and non-irritating to the wearer's skin. The absorbent core 50 can be formed by a single layer material or a plurality layers of materials. The absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; absorbent gelling materials; or any equivalent material or combinations of materials, or mixtures of these. In one preferred embodiment, the absorbent core is an air laid tissue material.

In a preferred embodiment, the absorbent core 50 preferably comprises a multi-bonded air laid nonwoven material. In this embodiment, this multi-bonded air laid nonwoven material comprises about 52% cellulose fibers, about 20% bi-component fibers, about 25% superabsorbent hydrogel-forming material (or absorbent gelling material) particles, and about 3% latex binder. The absorbent core 50 preferably has a basis weight of about 150 g/m2, including the particles of absorbent gelling material. Preferably, this multi-bonded air laid nonwoven absorbent core 50 is formed by depositing three streams of cellulose and bi-component fibers, with absorbent gelling material particles laid down with the last stream of fibers to form the bottom portion of the absorbent core. A preferred multi-bonded air laid nonwoven material is obtained in roll form from BBA (China) Airlaid Co. Ltd., Tianjin, China, under the code No. B888.M.150S17.

In a preferred embodiment, the garment facing surface 24 of the absorbent core 50 is covered with an color insulation layer (not shown in Figs.) which has a low light transmittance. Preferably, the color insulation layer is an additional later which is disposed between the absorbent core 50 and the garment contacting layer 40 (not shown in Figs.). The use of the color insulation layer is particularly preferred in the embodiment where the garment contacting layer 40 has a high second light transmittance (LT2) since the color insulation layer can hide the body fluids which are absorbed by the absorbent core 50 and may be seen by users through the garment contacting layer 40. Preferred materials for the color insulation layer include, but not limited to, a thin plastic film, a nonwoven web and a tissue (or other paper material). One preferred material for the color insulation layer is an air laid tissue material which is mixed with a titanium dioxide.

The absorbent core 50 is preferably joined with the body contacting layer 30, the garment contacting layer 40, or both in any manner as is known by attachment means such as those well known in the art. The garment contacting layer 40 and/or the body contacting layer 30 may be joined to the absorbent core 50 or to each other by a uniform continuous layer of adhesive, a patterned layer of adhesive, or an array of separate lines, spirals, or spots of adhesive.

The sanitary napkins 20 and 21 can generally have any thickness including relatively thick, intermediate thickness, relatively thin, or even very thin (or "ultra thin"). Preferred "ultra-thin" sanitary napkins which preferably have a caliper of less than about 3 mm are described in U.S. Pat. Nos. 4,950,264 and 5,009,653 issued to Osborn. The embodiments of the sanitary napkins 20 and 21 shown in FIGS. 1-4 are examples of an ultra-thin sanitary napkin. The sanitary napkins 20 and 21 may also be relatively flexible, so that they are comfortable for the wearer.

In a preferred embodiment, in particular for a thicker sanitary napkin, the body contacting layer 30 and the absorbent core 50 can be provided with embossed channels. The pattern of embossed channels typically include a continuous line(s) which can be straight and/or curved. The embossed channels can have any pattern known in the art. One preferred pattern of embossed channels is shown by the reference numbers 80 and 82 in FIG. 1. Other preferred embossed channels are disclosed in, for example, U.S. Pat. No. 5,795,345 issued to Mizutani et al. on Aug. 18, 1998; GB 2345449 B issued on May 9, 2001; and WO 96/07674 issued on Mar. 23, 1995.

Additionally or in an alternative preferred embodiment, the body contacting layer 30 is joined to the absorbent core 50 (or the secondary topsheet if exists) by a fusion bond (i.e., an application of heat/pressure). The pattern of the fusion bond can include a continuous line(s) and/or a number of discrete portion of fusion bonds. Any pattern known in the art can be applied. One preferred pattern of fusion bond is also shown by the reference numbers 80 and 82 in FIG. 1.

The fusion bond can be accomplished by heat and/or pressure bonds, ultrasonic bonds, dynamic mechanical bonds, and the like. Pressure can be applied in any suitable manner, such as by moving the components to be bonded between counter-rotating rolls, placing the materials on an anvil and forcing a platen down on the materials, applying vacuum pressure, and the like. A preferred design for the fusion bond is disclosed in U.S. Pat. No. 6,231,555 B1 issued to Lynard et al. on May 15, 2001.

The garment facing surface 24 of the sanitary napkin 20 (or the garment contacting layer 40) preferably includes fasteners for attaching the sanitary napkin 20 to the wearer's undergarment. Such fasteners include a central pad fastener 70 and a flap fastener 46. The central pad fastener 70 is adapted to secure the sanitary napkin 20 to the crotch region of an undergarment. Any types of fasteners known in the art, such as adhesive fasteners and mechanical fasteners can be used. A preferred central pad fastener 70 is a pressure-sensitive adhesive. In a preferred embodiment, the central pad fastener 70 includes a pair of spaced apart longitudinally-oriented strips or zones of adhesive that are centered about the longitudinal centerline L (not shown in Figs.).

The garment facing surface of the flaps 44, adjacent the distal edges of the flaps 44, is preferably provided with a flap fastener 46. The flap fastener 46 is used to assist in maintaining the flaps 44 in position after they are wrapped around the edge of the crotch portion of the undergarment. A preferred flap fastener 46 is a pressure-sensitive adhesive. The flaps 44 can be maintained in position by attaching the flaps 44 to the undergarment, or to the opposing flap.

The adhesive fasteners 70 and 46 are respectively covered by removable release liners, i.e., a central pad release liner 72 and a flap release liner 48. These release liners 72 and 48 are provided to protect the adhesive fasteners 70 and 46 before use. They also prevent the adhesive fasteners 70 and 46 from sticking to extraneous surfaces prior to use.

The sanitary napkin 20 is preferably wrapped by a wrapper sheet (not shown in Figs.). The wrapper sheet can be made from any suitable material. The wrapper sheet is preferably manufactured from a thin flexible material which is liquid impermeable so that the wrapper sheet will be suitable for wrapping and disposing of a used sanitary napkin 20. Preferred wrapper sheet materials include a polyethylene film and a nonwoven web. A preferred design for sanitary napkins is disclosed in U.S. Pat. No. 6,074,376 issued to Mills on Jun. 13, 2000.

Preferably, in the embodiments where the graphic 65 can be seen through the garment contacting layer 40, the wrapper sheet preferably has a light transmittance so that the graphic 65 can also be seen through both the garment contacting layer 40 and the wrapper sheet. In order to make the graphic be effectively seen, the material used for the wrapper sheet needs to have an appropriate range of light transmittance. In a preferred embodiment, the light transmittance of the wrapper sheet is at least about 10%, preferably in a range of about 45-100%, and more preferably in a range of about 80-100%. However, it is generally expected that the soiled sanitary napkin after use is wrapped by the wrapper sheet and then disposed. In order to prevent the body fluids absorbed by the soiled napkin from being seen through the wrapper sheet, the light transmittance of the wrapper sheet needs to be less than about 95%, preferably about 90%. Thus, there is a trade-off on the light transmittance of the wrapper sheet. In one preferred embodiment, the wrapper sheet is a spunbonded-meltblown-spunbonded (SMS) nonwoven which is available form Toray Saehan Inc., Korea, under Code No. SH-SMS 15 gms. The light transmittance of this wrapper sheet is about 88%.

Figure 5:
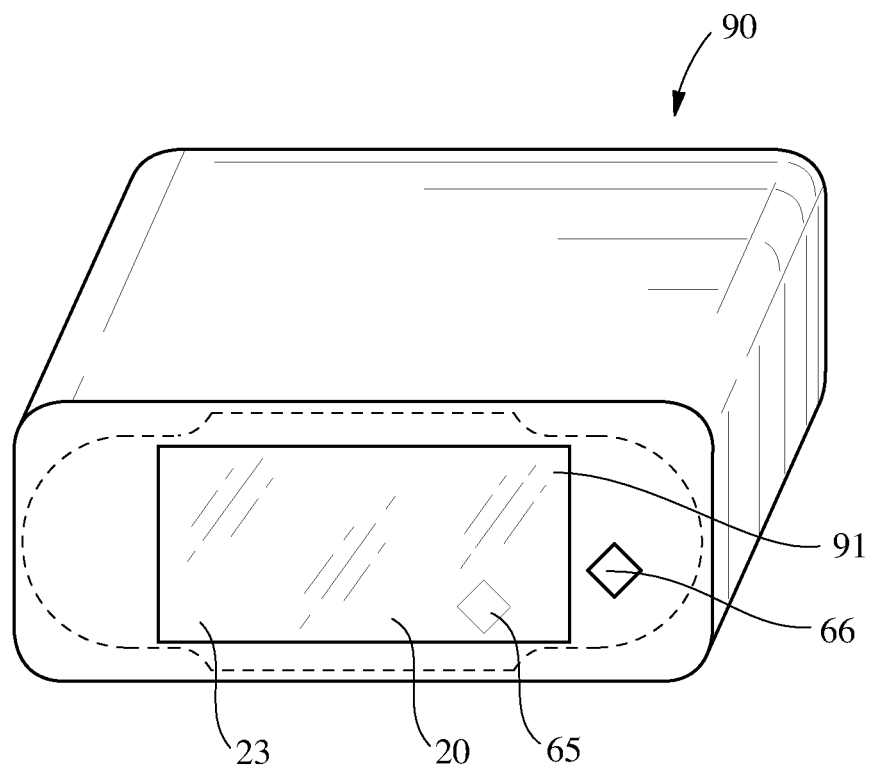
FIG. 5 is a perspective view of a package of a plurality of sanitary napkins.

As shown in FIG. 5, preferably, sanitary napkins (each wrapped by the wrapper sheet 23) 20 or 21 are stacked, compressed and contained in a package 90 such as a bag of polymeric film which preferably has a transparent portion(s) 91 (or window(s)) showing the graphic 65 of the sanitary napkins 20 or 21 therethough. A graphic(s) 66 common to the graphic 65 is preferably printed on the bag 90, thus users (or consumers) can see the common graphics 65, 66 on the bag 90 and the sanitary napkins 20 or 21 through the transparent portion(s) 91.

TEST METHODS

This section describes one preferred method for determining the light transmittance and the Hunter Lab Total Color Difference (HLTCD) of a sanitary napkin. It should be noted that other method known in the art for determining the light transmittance and/or the HLTCD can be applicable.

I. Light Transmittance (LT)

A light transmittance analyzer is preferably used for determining the light transmittance of a sample sheet material. A preferred light transmittance analyzer is available from Nomura Shoji Co., Ltd., Tokyo, Japan, under Trade Name "Formation Tester" and Code No. FMT-2000. This light transmittance analyzer includes a light source which has a Halogen lamp (12V, 75 W), a sample holder table having an open window, a CCD camera (256×243 pixels), and a computer. The light source is placed away from one side of the sample holder table, while the CCD camera is placed away from the other side of the sample holder table. The distance between the lens of the CCD camera and the sample holder table is about 415 mm. The open area of the window is adjusted so that its effective open area has a square of 40×45 mm.

In the measurement, the Halogen lamp turns on. When no sample sheet material is held by the sample holder table, the reference light volume (Vr) is measured by the CCD camera and recorded by the computer. A sample sheet material is held by the sample holder table so that it receives the light irradiated from the Halogen lamp in the effective open area. The light passes through the sample sheet material and reaches the CCD camera. The sample light volume (Vs) is then measured by each pixel of the CCD camera and recorded by the computer. This process is repeated for one sample sheet material at least three times and the average values of the light volumes (Vrav and Vsav) are calculated and recorded by the computer. The computer then calculates the light transmittance (LT) by the following formula:

$$LT = (V\text{sav}/V\text{rav}) \times 100 (\%) \quad (1)$$

II. Hunter Lab Total Color Difference (HLTCD)

A colorimeter is preferably used for determining the HLTCD of a sample material. A preferred colorimeter is available from Hunter Associates Laboratory, VA, US, under Trade Name "ColorQuest 45/0" and Code No. DP-9000. The measurement and calculation for the HLTCD is based on the condition which is defined by International Commission on Illumination (CIE) and registered as ASTM Method E308, wherein Observer 2°, Illuminant C, and a sample (circle) diameter of 1 inch.

This colorimeter includes a light source for Illuminant C (i.e., an approximation of average daylight having a correlated color temperature of about 6770 K), a sample holder, a photo detector which includes a multi-celled photo-detector diode array, and a computer.

In the measurement, a sample material is held on the sample holder. The sample material is illuminated by the light source with an incident angle of about 45°. The reflection light which is reflected from the sample material is received by the photo detector. The reflection light detected by the photo detector is converted to a lightness (L), a redness-greenness (a) and an yellowness-blueness (b) in response to the reflection light.

This measurement is conducted on each of two sample materials or two portions of one material to be compared by the above process. Thus, two sets of photo data (L1, a1, b1) and (L2, a2, b2) are obtained. These data are obtained as average data by repeating the above measurement at least three times for one material (or one portion). The HLTCD (ΔE) is then obtained by the following formulas:

$$\Delta L = L1 - L2 \quad (2)$$

$$\Delta a = a1 - a2 \quad (3)$$

$$\Delta b = b1 - b2 \quad (4)$$

$$\Delta E = \sqrt{(\Delta L^2 + \Delta a^2 + \Delta b^2)} \quad (5)$$

These data are calculated and recorded by the computer.

EXAMPLES

Table I shows data of the light transmittance obtained from sample materials (Sample Nos. 1-7) which can be used for both the body contacting layer 30 and the garment contacting layer 40.

TABLE I

| Sample No. | Material | Code No. | Supplier | LT |
|---|---|---|---|---|
| 1 | PE film | TF-FC-0001 (8 piles) | Thong Fook Plastics Ind. | 9.8 |
| 2 | PE film | TF-FC-0001 | Thong Fook Plastics Ind. | 47.3 |
| 3 | PE film | DH215 white 73 | Clopay Plastic Products Company | 69.4 |
| 4 | PE film | X-27121 | Tredegar Film Products | 73.4 |
| 5 | PP SMS nonwoven | SH-SMS 15 gsm | Toray Saehan Inc. | 88.4 |
| 6 | PP/PE bico spunbond nonwoven | LB7120 | Chisso Corporation | 90.1 |
| 7 | PE film | TF-FC-0003 | Thong Fook Plastics Ind. | 96.5 |

Table II shows sample materials (Sample Nos. 11-15) which are used for the HLTCD measurement. It should be noted that Sample No. 11 is preferably used for the absorbent core 50, Sample Nos. 12 and 13 are preferably used for the garment contacting layer 40, and Sample Nos. 14 and 15 are preferably used for the graphic protection layer 34. However, it should also be noted that Samples Nos. 12-15 can be used for any layer of the body contacting layer 30, the graphic protection layer 34 and the garment contacting layer 40, if desired.

TABLE II

| Sample No. | Material | Code No. | Supplier |
|---|---|---|---|
| 11 | Multi-bonded air laid nonwoven absorb. core | B888.M.150S17 | BBA (China) Airlaid Company Ltd. |
| 12 | PE film | TF-FC-0001 | Thong Fook Plastics Ind. |
| 13 | PE film | X-27121 | Tredegar Film Products |
| 14 | PP/PE bico spunbond nonwoven | LB7120 | Chisso Corporation |
| 15 | PP/PE bico spunbond nonwoven | LB7160 | Chisso Corporation |

Table III shows data of the HLTCD obtained from some combinations (i.e., Sample Nos. 21-24) of the sample materials in Table II. It should be noted that these combinations show preferred examples for the absorbent core 50 and the body contacting layer 30.

TABLE III

| Sample No. | Core Region | Outer Region | HLTCD (ΔE) |
|---|---|---|---|
| 21 | Sample Nos. 11 and 13* | Sample No. 12 | 14.4 |
| 22 | Sample Nos. 11 and 13* | Sample No. 15 | 28.8 |
| 23 | Sample Nos. 11 and 13* | Sample No. 14 | 49.5 |
| 24 | Sample Nos. 11 and 12* | Sample No. 14 | 50.1 |

*note: Sample No. 11 is disposed beneath the other sample material.

It is understood that the examples and embodiments described herein are for illustrative purpose only and that various modifications or changes will be suggested to one skilled in the art without departing from the scope of the present invention.

What is claimed is:

1. An absorbent article, comprising:
   a. a longitudinal centerline;
   b. a body contacting layer;
   c. a garment contacting layer;
   d. an absorbent core disposed between the body contacting layer and the garment contacting layer;
   e. an article core region;
   f. a pair of flaps extending from the article core region to define respective article outer regions that terminate at a lateral edge; and
   g. a graphic associated with the garment contacting layer;
   h. wherein the body contacting surface comprises:
      i. a topsheet associated with the article core region, the topsheet not extending outwardly to the lateral edges; and
      ii. a graphic protection layer in the form of a discrete strip of material disposed on each of the article outer regions, wherein each of the strips of material overlays a longitudinal side edge of the topsheet and comprises an inner edge that does not extend inwardly all the way to the longitudinal centerline; and
   i. wherein the graphic is visible through the discrete strips of material in the article outer regions.

2. The absorbent article of claim 1, wherein the topsheet comprises an apertured plastic film.

3. The absorbent article of claim 1, wherein the topsheet comprises a nonwoven web.

4. The absorbent article of claim 1, wherein the topsheet comprises an apertured plastic film and each of the discrete strips of material comprises a nonwoven web.

5. The absorbent article of claim 1, wherein the topsheet comprises a nonwoven web and each of the discrete strips of material comprises a nonwoven web.

6. The absorbent article of claim 1, wherein each of the discrete strips of material comprises synthetic fibers.

7. The absorbent article of claim 1, wherein each of the discrete strips of material is hydrophobic.

8. The absorbent article of claim 1, wherein the graphic is printed on the body facing surface of the garment contacting layer.

9. The absorbent article of claim 1, wherein the graphic comprises inner graphic portions that are positioned inward from the article outer regions and underneath the absorbent core, and wherein the graphic portions are only visible when viewing a garment facing surface of the garment contacting layer.

10. The absorbent article of claim 1, wherein the topsheet comprises embossed channels formed therein.

11. The absorbent article of claim 1, further comprising an acquisition layer disposed between the topsheet and the absorbent core.

12. The absorbent article of claim 1, wherein the article is a sanitary napkin or a pantiliner.

13. The absorbent article of claim 1, wherein the article is an incontinence pad.

14. An absorbent article, comprising:
 a. a longitudinal centerline;
 b. a body contacting layer;
 c. a garment contacting layer;
 d. an absorbent core disposed between the body contacting layer and the garment contacting surface;
 e. an article core region;
 f. a pair of flaps extending from the article core region to define respective article outer regions that terminate at a lateral edge; and
 g. wherein the body contacting surface comprises:
  i. a topsheet associated with the article core region, the topsheet not extending outwardly to the lateral edges; and
  ii. a discrete strip of material disposed on each of the article outer regions, wherein each of the strips of material overlays a longitudinal side edge of the topsheet and comprises an inner edge that does not extend inwardly all the way to the longitudinal centerline; and
 h. a graphic associated with a garment facing surface of the body contacting layer that is coincident with the article core region, wherein the graphic is visible when viewing a body facing surface of the body contacting layer.

15. The absorbent article of claim 14, wherein the topsheet comprises an apertured plastic film.

16. The absorbent article of claim 14, wherein the topsheet comprises a nonwoven web.

17. The absorbent article of claim 14, wherein the topsheet comprises an apertured plastic film and each of the discrete strips of material comprises a nonwoven web.

18. The absorbent article of claim 14, wherein each of the discrete strips of material comprises synthetic fibers.

19. The absorbent article of claim 14, wherein each of the discrete strips of material is hydrophobic.

20. The absorbent article of claim 14, wherein the graphic is printed on the garment facing surface of the body contacting layer.

21. The absorbent article of claim 14, wherein the topsheet comprises embossed channels formed therein.

22. The absorbent article of claim 14, further comprising an acquisition layer disposed between the topsheet and the absorbent core.

23. The absorbent article of claim 14, wherein the article is a sanitary napkin or a pantiliner.

24. The absorbent article of claim 14, wherein the article is an incontinence pad.

25. An absorbent article, comprising:
 a. a longitudinal centerline;
 b. a body contacting layer comprising an apertured formed film, the body contacting layer comprising a body facing surface and a garment facing surface;
 c. a garment contacting layer comprising a body facing surface and a garment facing surface;
 d. an absorbent core disposed between the body contacting layer and the garment contacting surface;
 e. a nonwoven web only partially overlaying outer regions of the apertured formed film wherein a gap in the nonwoven web is coincident with a portion along the longitudinal centerline; and
 f. a graphic disposed between the body facing surface of the body contacting layer and the garment facing surface of the garment contacting layer so that the graphic is positioned internal to the article at a depth that is at least a thickness of the nonwoven web plus the thickness of the apertured formed film, wherein the graphic is visible when viewing a body facing surface of the body contacting layer.

26. An absorbent article, comprising:
 a. a longitudinal centerline;
 b. a body contacting layer;
 c. a garment contacting layer;
 d. an absorbent core disposed between the body contacting layer and the garment contacting layer;
 e. an article core region centrally located and coincident with the longitudinal centerline;
 f. opposing article outer regions laterally outward from the article core region;
 g. wherein the body contacting layer comprises an apertured film;
 h. wherein the apertured film comprises ink on a garment facing side of the apertured film in the opposing article outer regions;
 i. wherein a fibrous material is disposed over the apertured film in the opposing article outer regions, the fibrous material comprising natural fibers, synthetic fibers, or a combination of natural and synthetic fibers; and
 j. wherein the ink can be seen through the apertured film and the fibrous material in the opposing article outer regions.

27. The absorbent article of claim 26, wherein ink is not visible in the article core region so that the only visible ink is in the opposing article outer regions.

* * * * *